(12) United States Patent
Haus (10) Patent No.: US 9,662,186 B2
(45) Date of Patent: May 30, 2017

(54) DENTAL COMPONENT WITH METAL ADAPTER

(71) Applicant: NOBEL BIOCARE SERVICES AG, Kloten (CH)

(72) Inventor: Adrian Haus, Zürich (CH)

(73) Assignee: Nobel Biocare Services AG, Kloten (CH)

( * ) Notice: Subject to any disclaimer, the term of this patent is extended or adjusted under 35 U.S.C. 154(b) by 32 days.

(21) Appl. No.: 14/654,440

(22) PCT Filed: Dec. 17, 2013

(86) PCT No.: PCT/EP2013/003806
§ 371 (c)(1),
(2) Date: Jun. 19, 2015

(87) PCT Pub. No.: WO2014/095033
PCT Pub. Date: Jun. 26, 2014

(65) Prior Publication Data
US 2015/0342708 A1    Dec. 3, 2015

(30) Foreign Application Priority Data
Dec. 21, 2012 (GB) .................................. 1223205.4

(51) Int. Cl.
*A61C 8/00* (2006.01)

(52) U.S. Cl.
CPC .......... *A61C 8/0062* (2013.01); *A61C 8/0066* (2013.01); *A61C 8/0068* (2013.01); *A61C 8/0054* (2013.01)

(58) Field of Classification Search
CPC combination set(s) only.
See application file for complete search history.

(56) References Cited

U.S. PATENT DOCUMENTS

| 2,721,387 A | 10/1955 | Ashuckian |
| 4,259,072 A | 3/1981 | Hirabayashi et al. |
| (Continued) | | |

FOREIGN PATENT DOCUMENTS

| AU | A-75458/96 | 6/1997 |
| CH | 692 542 | 7/2002 |
| (Continued) | | |

OTHER PUBLICATIONS

Brodbeck, Urs, "The ZiReal Post: A New Ceramic Implant Abutment," J Esthet Restor Dent 15:10-24, 2003.
(Continued)

*Primary Examiner* — Jan Christopher Merene
(74) *Attorney, Agent, or Firm* — Knobbe, Martens, Olson & Bear LLP (57) ABSTRACT

The present invention relates to a dental component (10) for attachment to a dental implant (46), wherein the dental component comprises: a component body (12) including at least one concave recess (38); and a metal adapter (14) removably attachable to the component body, wherein the metal adapter includes at least one convex lobe (16) adapted to abut against the at least one concave recess in the component body for preventing rotation between the component body and the metal adapter, and wherein said at least one convex lobe extends apically of an apical end (34) of the component body when the metal adapter is attached to the component body.

13 Claims, 6 Drawing Sheets

(56) References Cited

U.S. PATENT DOCUMENTS

| | | |
|---|---|---|
| 4,560,353 A | 12/1985 | Schulte et al. |
| 4,575,340 A | 3/1986 | Lustig |
| 4,746,293 A | 5/1988 | Lundgren et al. |
| 4,758,161 A | 7/1988 | Niznick |
| 4,763,788 A | 8/1988 | Jürnéus et al. |
| 4,824,372 A | 4/1989 | Jürnéus et al. |
| 4,846,683 A | 7/1989 | Lazzara et al. |
| 4,850,870 A | 7/1989 | Lazzara et al. |
| 4,850,873 A | 7/1989 | Lazzara et al. |
| 4,854,872 A | 8/1989 | Detsch |
| 4,856,994 A | 8/1989 | Lazzara et al. |
| 4,872,839 A | 10/1989 | Brajnovic |
| 4,904,187 A | 2/1990 | Zingheim |
| 4,955,811 A | 9/1990 | Lazzara et al. |
| 4,988,297 A | 1/1991 | Lazzara et al. |
| 4,988,298 A | 1/1991 | Lazzara et al. |
| 5,000,686 A | 3/1991 | Lazzara et al. |
| 5,006,069 A | 4/1991 | Lazzara et al. |
| 5,015,186 A | 5/1991 | Detsch |
| 5,022,860 A | 6/1991 | Lazzara et al. |
| 5,030,096 A | 7/1991 | Hurson et al. |
| 5,035,619 A | 7/1991 | Daftary |
| 5,040,982 A | 8/1991 | Stefan-Dogar |
| 5,040,983 A | 8/1991 | Binon |
| 5,064,373 A | 11/1991 | Staubli et al. |
| 5,064,375 A | 11/1991 | Jürnéus et al. |
| 5,069,622 A | 12/1991 | Rangert et al. |
| 5,071,345 A | 12/1991 | Rosen |
| 5,071,351 A | 12/1991 | Green, Jr. et al. |
| 5,073,111 A | 12/1991 | Daftary |
| 5,082,442 A | 1/1992 | Rosen |
| 5,087,200 A | 2/1992 | Brajnovic et al. |
| 5,100,323 A | 3/1992 | Friedman et al. |
| 5,105,690 A | 4/1992 | Lazzara et al. |
| 5,106,300 A | 4/1992 | Voitik |
| 5,125,839 A | 6/1992 | Ingber et al. |
| 5,125,841 A | 6/1992 | Carlsson et al. |
| 5,135,395 A | 8/1992 | Marlin |
| 5,145,371 A | 9/1992 | Jürnéus |
| 5,145,372 A | 9/1992 | Daftary et al. |
| 5,152,687 A | 10/1992 | Amino |
| 5,154,612 A | 10/1992 | Carlsson et al. |
| 5,169,309 A | 12/1992 | Staubli et al. |
| 5,188,800 A | 2/1993 | Green, Jr. et al. |
| 5,209,659 A | 5/1993 | Friedman et al. |
| 5,209,666 A | 5/1993 | Balfour et al. |
| 5,213,502 A | 5/1993 | Daftary |
| 5,238,405 A | 8/1993 | Marlin |
| 5,246,370 A | 9/1993 | Coatoam |
| 5,259,759 A | 11/1993 | Jorneus et al. |
| 5,269,685 A | 12/1993 | Jorneus et al. |
| 5,281,140 A | 1/1994 | Niznick |
| 5,282,746 A | 2/1994 | Sellers et al. |
| 5,292,252 A | 3/1994 | Nickerson et al. |
| 5,297,963 A | 3/1994 | Dafatry |
| 5,316,476 A | 5/1994 | Krauser |
| 5,334,024 A | 8/1994 | Niznick |
| 5,336,090 A | 8/1994 | Wilson, Jr. et al. |
| 5,338,196 A | 8/1994 | Beaty et al. |
| 5,344,457 A | 9/1994 | Pilliar et al. |
| 5,350,302 A | 9/1994 | Marlin |
| 5,368,483 A | 11/1994 | Sutter et al. |
| 5,417,568 A | 5/1995 | Giglio |
| 5,419,702 A | 5/1995 | Beaty et al. |
| 5,431,567 A | 7/1995 | Daftary |
| 5,439,380 A | 8/1995 | Marlin |
| 5,447,435 A | 9/1995 | Brodbeck |
| 5,476,383 A | 12/1995 | Beaty et al. |
| 5,492,471 A | 2/1996 | Singer |
| 5,564,921 A | 10/1996 | Marlin |
| 5,584,694 A | 12/1996 | Forsalm et al. |
| 5,658,147 A | 8/1997 | Phimmasone |
| 5,662,474 A | 9/1997 | Jürnéus et al. |
| 5,685,714 A | 11/1997 | Beaty et al. |
| 5,702,252 A | 12/1997 | Rogers et al. |
| 5,725,375 A | 3/1998 | Rogers |
| 5,741,267 A | 4/1998 | Jürnéus et al. |
| 5,829,977 A | 11/1998 | Rogers et al. |
| 5,873,720 A | 2/1999 | Jürnéus et al. |
| 5,873,722 A | 2/1999 | Lazzara et al. |
| RE36,126 E | 3/1999 | Beaty et al. |
| 5,904,483 A | 5/1999 | Wade |
| 5,934,906 A | 8/1999 | Phimmasone |
| 5,947,732 A | 9/1999 | Beaty et al. |
| 5,989,026 A | 11/1999 | Rogers et al. |
| 6,012,923 A | 1/2000 | Bassett et al. |
| 6,048,203 A | 4/2000 | Rosenberg |
| RE36,689 E | 5/2000 | Beaty et al. |
| 6,068,479 A | 5/2000 | Kwan |
| 6,152,737 A | 11/2000 | Beaty et al. |
| 6,159,008 A | 12/2000 | Kumar |
| 6,168,435 B1 | 1/2001 | Beaty et al. |
| 6,174,166 B1 | 1/2001 | Jürnéus |
| 6,196,842 B1 | 3/2001 | Jürnéus |
| 6,227,856 B1 | 5/2001 | Beaty et al. |
| RE37,227 E | 6/2001 | Brodbeck |
| 6,276,938 B1 | 8/2001 | Jürnéus et al. |
| 6,290,499 B1 | 9/2001 | Lazzara et al. |
| 6,343,930 B1 | 2/2002 | Beaty et al. |
| 6,358,050 B1 | 3/2002 | Bergstrom et al. |
| 6,382,977 B1 | 5/2002 | Kumar |
| 6,394,806 B1 | 5/2002 | Kumar |
| 6,394,809 B2 | 5/2002 | Rogers et al. |
| 6,419,489 B1 | 7/2002 | Jürnéus et al. |
| 6,561,805 B2 | 5/2003 | Kumar |
| 6,626,911 B1 | 9/2003 | Engman et al. |
| 6,644,969 B2 | 11/2003 | Kumar |
| 6,655,962 B1 | 12/2003 | Kennard |
| 6,733,291 B1 | 5/2004 | Hurson |
| 6,769,913 B2 | 8/2004 | Hurson |
| 6,827,575 B1 | 12/2004 | Jürnéus |
| 6,848,908 B2 | 2/2005 | Björn et al. |
| 6,896,517 B1 | 5/2005 | Björn et al. |
| 6,902,401 B2 | 6/2005 | Jürnéus et al. |
| 7,008,228 B2 | 3/2006 | Björn et al. |
| 7,108,510 B2 * | 9/2006 | Niznick ............ A61C 8/005 433/173 |
| 7,338,286 B2 | 3/2008 | Porter et al. |
| 7,363,239 B1 | 4/2008 | Andersson et al. |
| 7,484,959 B2 | 2/2009 | Porter et al. |
| 7,491,058 B2 | 2/2009 | Jürnéus et al. |
| 7,665,989 B2 | 2/2010 | Brajnovic et al. |
| 8,033,826 B2 * | 10/2011 | Towse ............... A61C 8/005 433/172 |
| 8,038,445 B2 | 10/2011 | Brajnovic et al. |
| 8,231,825 B2 | 7/2012 | Eriksson et al. |
| 8,272,871 B2 | 9/2012 | Hurson |
| 8,608,473 B2 | 12/2013 | Kennard |
| 8,747,112 B2 | 6/2014 | Brun |
| 8,805,658 B2 | 8/2014 | Pettersson et al. |
| 8,915,735 B1 | 12/2014 | Carlsson et al. |
| 9,125,708 B2 | 9/2015 | Carvalho et al. |
| 2002/0192620 A1 | 12/2002 | Jürnéus et al. |
| 2003/0104336 A1 | 6/2003 | Sethi et al. |
| 2003/0124488 A1 | 7/2003 | Gittleman |
| 2003/0162149 A1 | 8/2003 | Björn et al. |
| 2004/0038179 A1 * | 2/2004 | Kumar ............... A61C 8/008 433/173 |
| 2005/0019731 A1 | 1/2005 | Björn et al. |
| 2005/0065525 A1 | 3/2005 | Aringskog et al. |
| 2006/0008772 A1 | 1/2006 | Brajnovic et al. |
| 2006/0110706 A1 | 5/2006 | Jürnéus et al. |
| 2006/0246396 A1 | 11/2006 | Suttin et al. |
| 2007/0117066 A1 | 5/2007 | Jürnéus et al. |
| 2007/0281278 A1 | 12/2007 | Jürnéus et al. |
| 2008/0102420 A1 | 5/2008 | Porter et al. |
| 2008/0166682 A1 | 7/2008 | Björn et al. |
| 2008/0261175 A1 | 10/2008 | Hurson |
| 2009/0081612 A1 | 3/2009 | Jürnéus et al. |
| 2009/0130629 A1 | 5/2009 | Towse et al. |
| 2009/0136899 A1 | 5/2009 | Porter et al. |
| 2009/0239200 A1 | 9/2009 | Brajnovic et al. |
| 2009/0298013 A1 * | 12/2009 | Baruc ............... A61C 8/005 433/174 |

(56) References Cited

U.S. PATENT DOCUMENTS

| | | |
|---|---|---|
| 2010/0291509 A1 | 11/2010 | Berggren et al. |
| 2010/0297583 A1 | 11/2010 | Benzon et al. |
| 2010/0323327 A1 | 12/2010 | Eriksson et al. |
| 2011/0014586 A1 | 1/2011 | Jürnéus et al. |
| 2011/0060558 A1 | 3/2011 | Pettersson et al. |
| 2011/0123948 A1 | 5/2011 | Hinrichsen |
| 2011/0123953 A1 | 5/2011 | Jürnéus et al. |
| 2011/0183291 A1 | 7/2011 | Malo Carvalho et al. |
| 2012/0009545 A1 | 1/2012 | Eriksson et al. |
| 2012/0077150 A1 | 3/2012 | Goodman et al. |
| 2012/0191097 A1 | 7/2012 | Jürnéus et al. |
| 2012/0191103 A1 | 7/2012 | Jürnéus et al. |
| 2012/0295224 A1 | 11/2012 | Jürnéus et al. |
| 2012/0301850 A1 | 11/2012 | Sollberger et al. |
| 2012/0326343 A1 | 12/2012 | Eriksson et al. |
| 2013/0045463 A1 | 2/2013 | Lindstrom et al. |
| 2014/0011160 A1 | 1/2014 | Jürnéus et al. |
| 2014/0124374 A1 | 5/2014 | Eriksson et al. |
| 2014/0178836 A1 | 6/2014 | Haus et al. |
| 2014/0186797 A1 | 7/2014 | Haus |
| 2015/0230890 A1 | 8/2015 | Malo Carvalho et al. |
| 2015/0305836 A1* | 10/2015 | Fischer ................ A61C 8/0068 433/173 |

FOREIGN PATENT DOCUMENTS

| | | |
|---|---|---|
| DE | 27 17 506 | 5/1978 |
| DE | 32 24 112 | 2/1984 |
| DE | 34 44 780 | 6/1986 |
| DE | 38 25 601 | 3/1989 |
| DE | 41 27 839 | 3/1992 |
| DE | 42 30 009 | 1/1993 |
| DE | 101 29 684 A1 | 1/2003 |
| DE | 10 2009 057754 A1 | 6/2011 |
| EP | 0 377 068 B1 | 11/1992 |
| EP | 0 534 078 A1 | 3/1993 |
| EP | 0 320 024 B1 | 12/1993 |
| EP | 0 474 571 B1 | 4/1995 |
| EP | 0 477 644 B1 | 5/1996 |
| EP | 0 657 146 B1 | 4/1998 |
| EP | 1 269 932 A1 | 1/2003 |
| EP | 1 073 381 B1 | 9/2004 |
| EP | 0 786 966 B1 | 5/2006 |
| EP | 0 837 658 B1 | 4/2007 |
| EP | 1 021 997 B1 | 5/2007 |
| EP | 1 124 501 B1 | 6/2007 |
| EP | 2 025 302 A1 | 2/2009 |
| EP | 2 090 263 A1 | 8/2009 |
| EP | 2 127 612 A1 | 12/2009 |
| EP | 1 613 237 B1 | 2/2011 |
| EP | 1 419 746 B1 | 6/2011 |
| EP | 1 820 467 B1 | 7/2015 |
| GB | 1 305 478 | 1/1973 |
| GB | 2 213 065 | 8/1989 |
| GB | 2 487 553 | 8/2012 |
| WO | WO 93/02632 | 2/1993 |
| WO | WO 97/10770 | 3/1997 |
| WO | WO 00/24335 | 5/2000 |
| WO | WO 03/049636 | 6/2003 |
| WO | WO 2004/002358 | 1/2004 |
| WO | WO 2008/128757 | 10/2008 |
| WO | WO 2014/095034 | 6/2014 |

OTHER PUBLICATIONS

International Search Report for Application No. PCT/EP2013/003806 mailed on Mar. 19, 2014 in 4 pages [the ISR for the PCT Application of this US national phase application].

International Search Report for Application No. PCT/EP2013/003807 mailed on Apr. 9, 2014 in 5 pages [the ISR for the PCT Application of U.S. Appl. No. 14/654,407].

* cited by examiner

DENTAL COMPONENT WITH METAL ADAPTER

CROSS-REFERENCE TO RELATED APPLICATIONS

This application is a national stage application under 35 U.S.C. §371 of International Application No. PCT/EP2013/003806, filed on Dec. 17, 2013, which published in English as WO 2014/095033 A1 on Jun. 26, 2014 and which claims priority benefit of GB Patent Application No. 1223205.4 filed on Dec. 21, 2012.

The present invention relates a dental component comprising a metal adapter.

WO2004002358 A1 discloses a spacer with associated adapter designed to be fitted on an implant. The adapter comprises first and second portions designed to cooperate with the spacer and the implant, respectively, for securing the spacer on the implant. The adapter is completely enclosed by the spacer and the implant, and the first portion of the adapter can be designed with slits for forming resilient elements on said portion and/or with penetrating parts which, when the adapter and the spacer are joined together, are deformed as it penetrates into opposite parts in the spacer material. The spacer and the adapter can in this way be easily held together upon application to the implant and can be taken apart when completion work is performed on the spacer. The first portion has a hexagonal cross section, while the second portion is provided with outwardly projecting members, specifically three convex lobes. However, the abutment-implant contact surface of the spacer in WO02004002358 A1 may be somewhat small. Also, there can be some overall rotational play between the hexagonal first portion and the spacer on one hand, and the lobed second portion and the implant on the other hand.

The present invention is defined in the appended independent claims. Embodiments are defined in the appended dependent claims.

According to an aspect of the present invention, there is provided a dental component for attachment to a dental implant, the dental component comprising: a component body including at least one concave recess; and a metal adapter removably attachable to the component body, wherein the metal adapter includes at least one convex lobe adapted to abut against the at least one concave recess in the component body for preventing rotation between the component body and the metal adapter, and wherein said at least one convex lobe extends apically of an apical end of the component body when the metal adapter is attached to the component body. Said at least one convex lobe may be adapted to abut also against at least one corresponding concave recess in the dental implant for preventing rotation between the dental component and the dental implant. Hence, there is only one connection (the at least one lobe) on the adapter that fits into the implant as well to the component body, whereby the rotational play tolerances may be reduced.

The metal adapter may comprise at least one flexible arm with a protrusion adapted to press against a side wall and/or snap into a corresponding undercut (if there is any) of the component body for securing the metal adapter to the component body in the coronal-apical direction.

The component body may at its apical end have a recess including said at least one concave recess and said side wall, wherein the recess is surrounded by a dental implant contacting surface.

The at least one convex lobe and the at least one corresponding concave recess may consist of three convex lobes and concave recesses uniformly distributed in the circumferential direction of the dental component, wherein the at least one flexible arm consists of three flexible arms each having a protrusion, the three flexible arms being uniformly distributed in the circumferential direction of the dental component such that the each flexible arm is positioned between two of the convex lobes.

The metal adapter may be completely enclosed inside the component body and the dental implant.

The component body may comprise a screw channel passing through the component body and forming a first opening at a first end and a second opening at an apical end, and a screw seat proximal to the apical end of the screw channel for seating the head of a screw for the fixation of the dental component to the dental implant.

In one or more embodiments, the longitudinal axis of the screw channel at the first end does not match the longitudinal axis of the screw channel at the apical end.

The dental component may for example be an abutment.

The component body is adapted to support a dental restoration.

The component body may be full-contour part.

The component body may be ceramic.

According to another aspect of the present invention, the dental component is provided in combination with the dental implant.

According to yet another aspect of the present invention, there is provided a method of assembling a dental component for attachment to a dental implant, the dental component comprising: a ceramic component body including at least one concave recess, and a metal adapter removably attachable to the ceramic component body, wherein the metal adapter includes at least one convex lobe adapted to abut against the at least one concave recess in the ceramic component body for preventing rotation between the ceramic part and the metal adapter, which method comprises: attaching the metal adapter to the ceramic component body so that the at least one convex lobe of the metal adapter abuts against the at least one concave recess in the ceramic component body, whereby said at least one convex lobe extends apically of an apical end of the ceramic component body to serve also as an interface to the dental implant. This aspect may exhibit the same or similar features and/or technical effects as the previously discussed aspects, and vice versa.

These and other aspects of the present invention will now be described in more detail, with reference to the appended drawings showing currently preferred embodiments of the invention.

FIG. 1b is a cross-sectional view of the dental component in FIG. 1a.

FIG. 2b is a cross-sectional view of the metal adapter in FIG. 2a.

FIG. 2c is a side view of the metal adapter in FIG. 2a.

FIG. 2d is a top view of the metal adapter in FIG. 2a.

FIG. 3b is a cross-sectional side view of the component body in FIG. 3a.

FIG. 3c is a bottom view of the component body in FIG. 3a.

FIG. 4b is a cross-sectional view of the arrangement in FIG. 4a.

FIG. 5 is a top view of the implant in FIG. 4a.

Figure 1A:
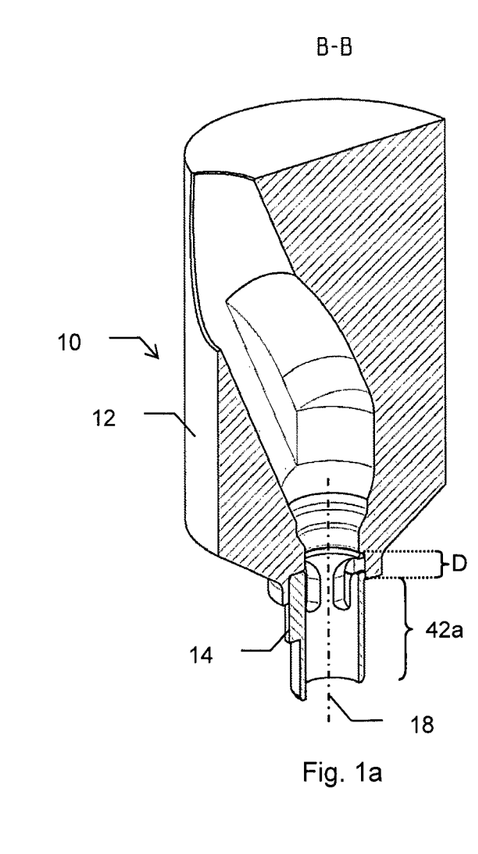
FIG. 1a is a perspective view of a dental component with a component body and a metal adapter according to an embodiment of the present invention.
Figure 1B:
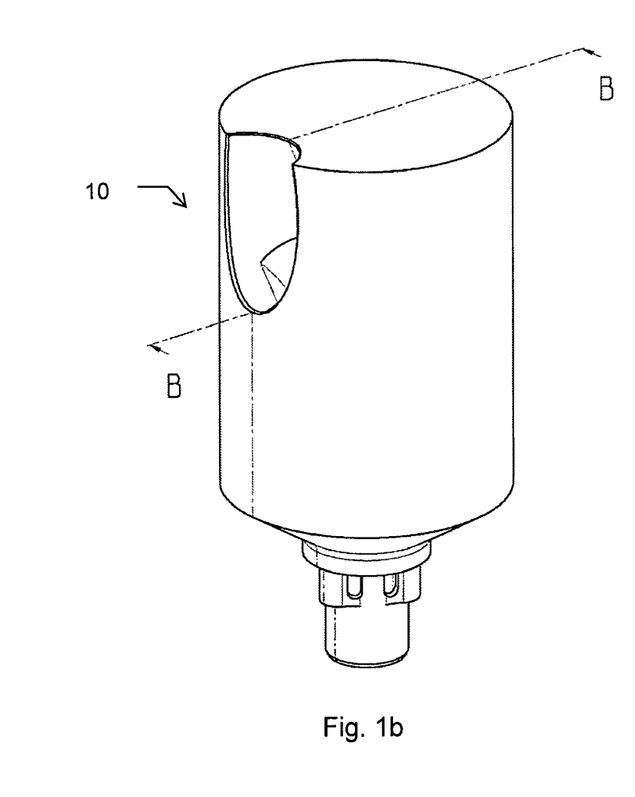

FIGS. 1a-1b show a dental component 10, for example an abutment (final or temporary), according to an embodiment of the present invention.

The dental component 10 comprises a coronal component body 12. The outer shape of the component body 12 in the figures may be schematic. The component body 12 may be adapted to support a dental restoration or a dental prosthesis, such as a single-unit restoration (crown) or a bridge. The restoration or prosthesis may for example be cemented to the component body 12. Alternatively, the component body of the present dental component may be a full-contour part. The component body 12 is preferably made entirely of ceramic material such as zirconia.

Alternatively, the component body 12 can be made of PEEK (polyether ether ketone), gold, etc.

The dental component 10 further comprises an apical metal adapter 14. The metal adapter 14 is also shown in FIG. 2. The metal adapter 14 is for example made of titanium or titanium alloy. The metal adapter 14 includes at least one convex lobe 16. The at least one convex lobe 16 is outwardly projecting, with respect to the central longitudinal axis 18 of the dental component 10/component body 12/metal adapter 14. The at least one convex lobe 16 extends substantially from the coronal end 20 of the metal adapter 14 and towards (but not necessarily all the way to) the apical end 22 of the metal adapter 14. The at least one convex lobe 16 extends substantially parallel to the longitudinal axis 18. The edge 24 of the metal adapter 14 at the coronal end 20 may be bevelled. Apically of the at least one convex lobe 16, the metal adapter 14 may comprise a substantially cylindrical portion 26. The metal adapter 14 further comprises a central bore 28. The bore 28 passes through the metal adapter 14, and forms a coronal opening 30a and an apical opening 30b. Specifically, the illustrated metal adapter 14 includes three convex lobes 16a-c. The three convex lobes 16a-c are uniformly distributed in the circumferential direction of the dental component 10.

Figure 3A:
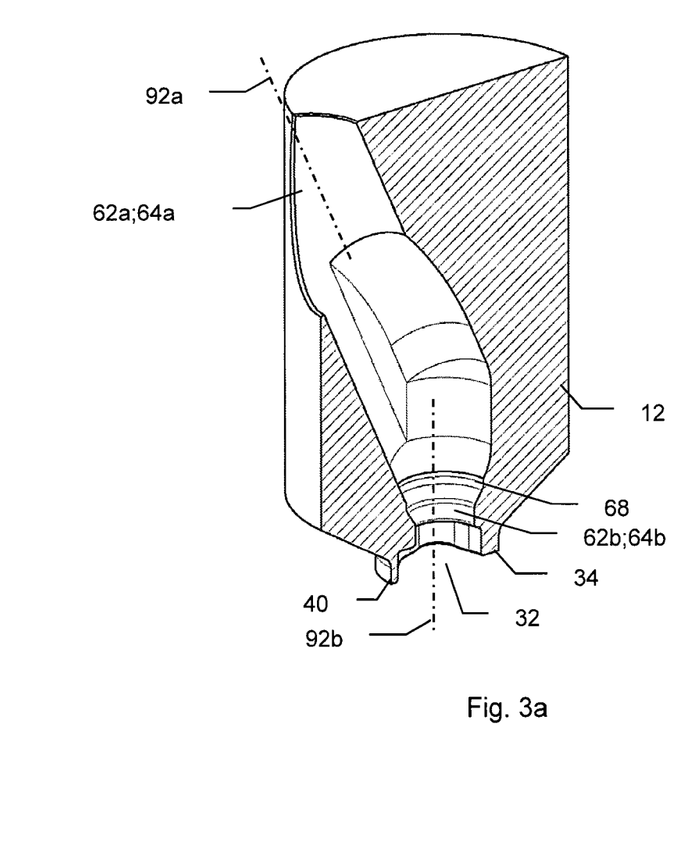
FIG. 3a is a cross-sectional perspective view of the component body of FIGS. 1a-1b.
Figure 3B:
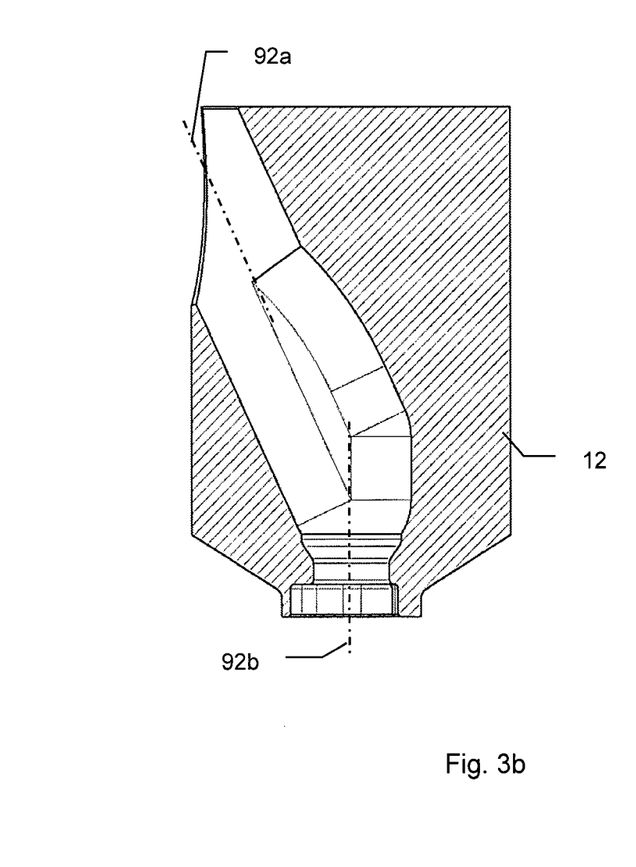
Figure 3C:
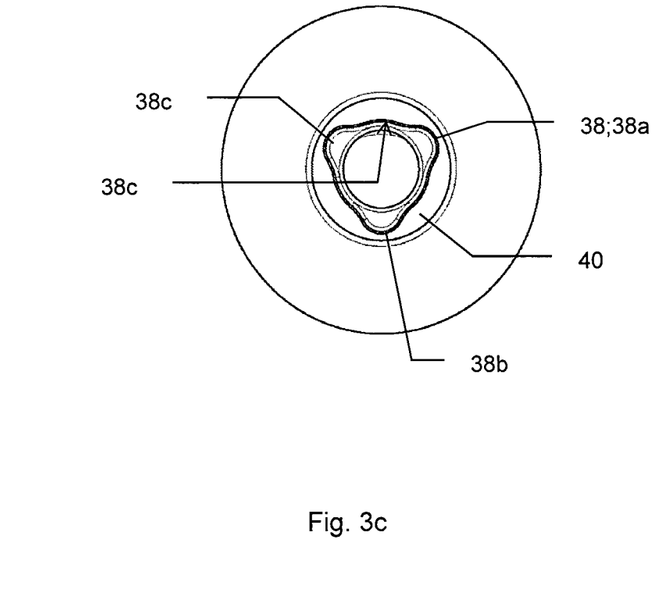

The component body 12 comprises a substantially central recess 32 provided at the apical end 34 of the component body 12, see FIGS. 3a-3c. The recess 32 in turn includes a side wall 36 and at least one concave recess 38 corresponding to the at least one convex lobe 16 of the metal adapter 14. The at least one convex lobe 16 is adapted to laterally abut against the at least one concave recess 38 for preventing rotation between the component body 12 and the metal adapter 14 when they are attached to each other. The recess 32 is surrounded by a circumferential apical surface 40, which preferably is flat in a plane perpendicular to the longitudinal axis 18. Specifically, the illustrated component body 12 includes three concave recesses 38a-c matching the convex lobes 16a-c. The three concave recesses 38a-c are uniformly distributed in the circumferential direction of the dental component 10.

Figure 4A:
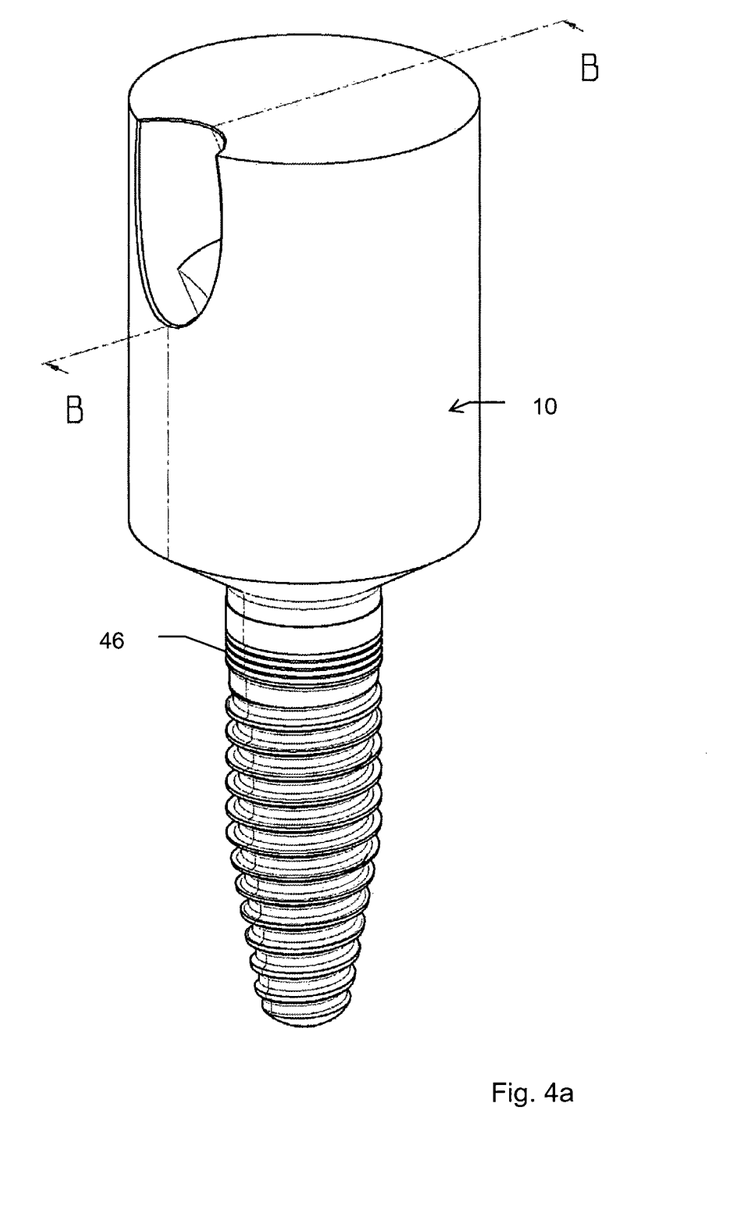
FIG. 4a is a perspective view of the dental component of FIGS. 1a-1b attached and fixed to a dental implant.
Figure 4B:
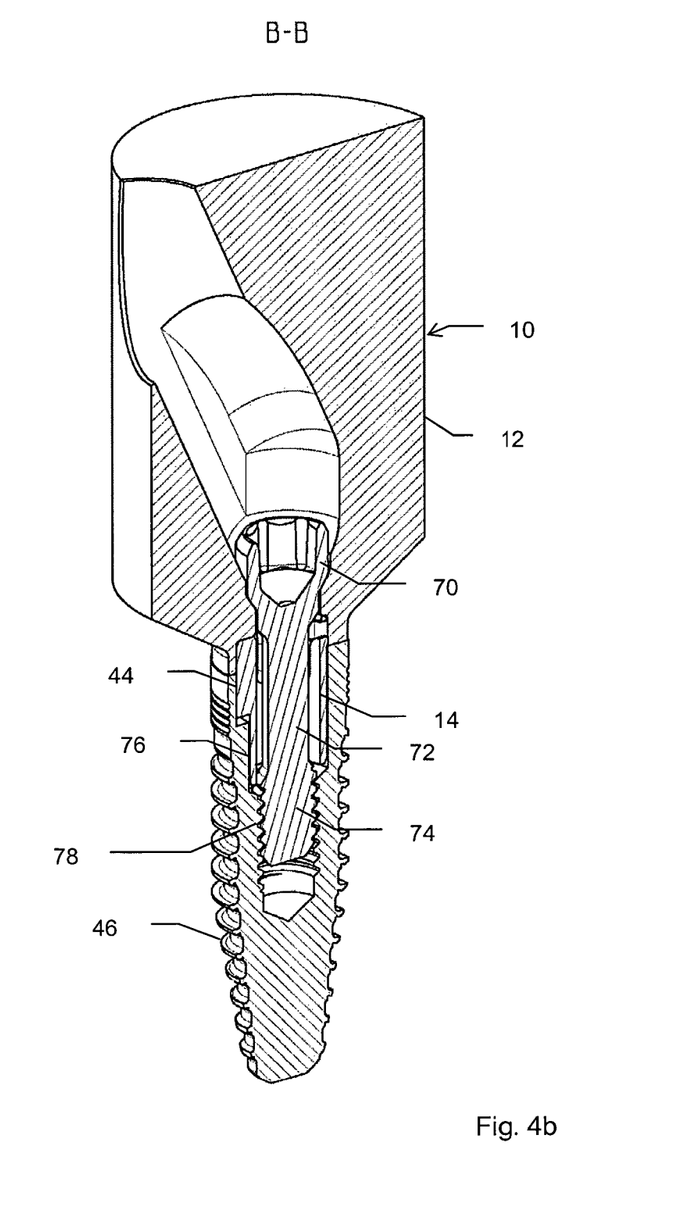
Figure 5:
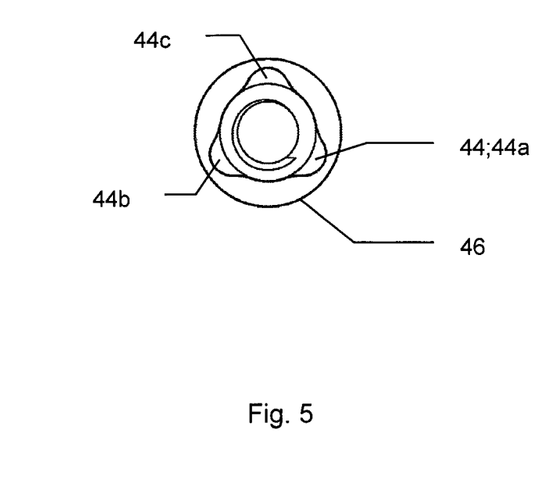

The dental component 10 is dimensioned so that the at least one convex lobe 16 extends uninterrupted and apically of the apical end 34 of the component body 12 when the metal adapter 14 is properly attached to the component body 12. Hence, the at least one convex lobe 16 has an exposed apical region 42a as shown in FIGS. 1a-1b, and another coronal region 42b received in the recess 32. To this end, the height H of the at least one convex lobe 16 is greater than the depth D of the recess 32, as seen in the direction of the longitudinal axis 18. As the metal adapter 14 is properly attached to the component body 12, the coronal end 20 of the metal adapter 14 abuts against the coronal/bottom surface 80 of the recess 32. The exposed region 42a of the at least one convex lobe 16 is adapted to abut laterally against at least one corresponding concave recess 44 of a dental implant 46 (as shown in FIG. 4), for preventing rotation between the metal adapter 14/dental component 10 and the dental implant 46. In the illustrated embodiment, the dental implant 46 includes three concave recesses 44a-c, see also FIG. 5. The three concave recesses 44a-c are preferably embodied in the same way as those in the so called internal tri-channel connection interface already included in several of Applicant's implants, for example NobelReplace with internal tri-channel connection. As the dental component 10 is attached to the implant 46, the circumferential apical surface 40 of the component body 12 abuts against a corresponding or greater coronal top surface 48 of the implant 46. This increased dental component 10/implant 46 contact surface over the solution disclosed in WO2004002358 A1 leads to better stress flow and improved strength. Also, the present invention decreases the rotational play tolerances at least by half over the solution disclosed in WO2004002358 A1, since there is only one connection (the at least one lobe 16) on the adapter 14 that fits into the implant 46 as well to the component body 12. In addition to the at least one concave recess 44, the dental implant 46 comprises a cylindrical chamber 76 matching the cylindrical portion 26 and arranged apically of the at least one concave recess 44. The implant 46 further comprises an internally threaded portion 78 arranged apically of the cylindrical chamber 76 (FIG. 4b).

The metal adapter 14 is removably attachable to the component body 12, so that the metal adapter 12 repeatedly may be attached/detached. To this end, the metal adapter 14 may comprise at least one flexible arm 52 with a protrusion 50. The at least one flexible arm 52 may for instance be formed by a cut out in the side wall of the metal adapter 14. The at least one arm 52 extends in a direction away from the apical end 22 of the metal adapter 14, and it is generally parallel to the longitudinal axis 18. The protrusion 50 is provided at the coronal free end of the flexible arm 52. The at least one protrusion 50 is outwardly directed. Outwardly here means substantially away from the central longitudinal axis 18. The at least one protrusion 50 may for instance project radially away from the axis 18. The at least one protrusion 50 may have a limited extent in the axial direction. In other words, it has a defined height. Each flexible arm-protrusion combination may also be referred to as a latch.

Figure 2A:
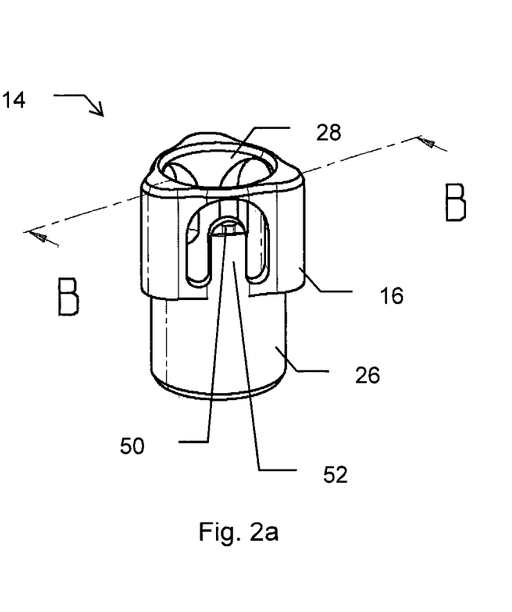
FIG. 2a is a perspective view of the metal adapter of FIGS. 1a-1b.
Figure 2B:
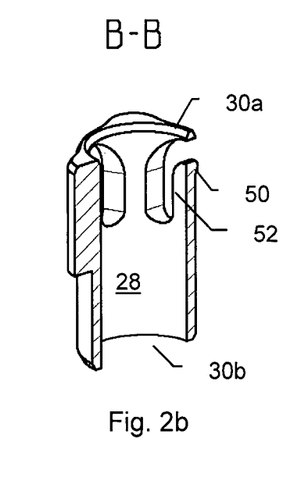
Figure 2C:
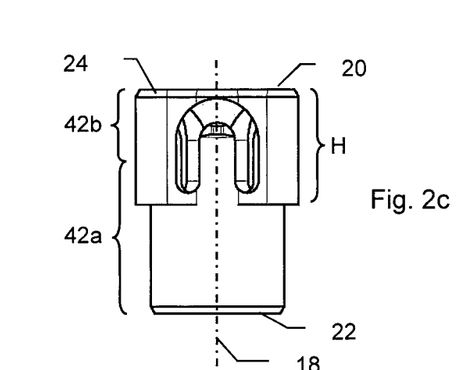
Figure 2D:
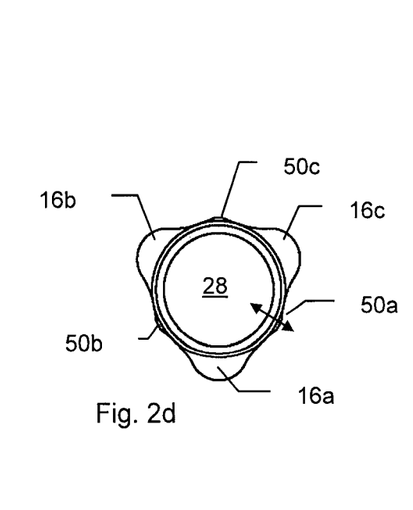

The at least one arm 52 is flexible so that the free end with the protrusion 50 can move or flex radially (perpendicular to the longitudinal axis 18), as indicated by the arrow in FIG. 2d. The flexibility of the at least one arm 52 may be achieved and controlled by selecting suitable dimensions of the arm 52 given what material the adapter 14 is made of. The at least one flexible arm 52 is arranged substantially in level with the at least one convex lobe 16. In the illustrated embodiment, there are three flexible arms 52a-c each with a protrusion 50a-c. The three flexible arms 52a-c are uniformly distributed in the circumferential direction of the dental component 10 such that the each protrusion-flexible arm combination is positioned between two of the convex lobes 16a-c. The component body 12 may optionally comprises at least one undercut (not shown) in the recess 32, which at least one undercut matches the at least one protrusion 50 of the metal adapter 14.

When the component body 12 and the metal adapter 14 are mated, the protrusions 50 press against the side wall 36 between the concave recesses 38 of the recess 32, whereby the metal adapter 14 is attached axially (coronal-apical direction) to the component body 12 by means of friction-fit and/or press-fit. With mainly elastic deformation of the metal arms 52, the metal adapter 14 may be attached to and removed from the component body 12 several times. The metal adapter 14 may be attached to (and removed from) the component body 12 manually, without the use of tools or additional fastening means such as glue, screws, bolts, etc. In case the recess 32 also comprises said at least one undercut, the protrusions 50 may be received therein, whereby snap-locking may occur.

The component body 12 further comprises a screw channel 60. The screw channel 60 passes through the component body 12, and forms a first opening 62*a* at a first end 64*a* of the screw channel 60 and a second opening 62*b* at a second (apical) end 64*b* of the screw channel 60. The second opening 62*b* is in the coronal/bottom surface 80 of the recess 32 of the component body 12.

The screw channel 60 may be straight (not shown). Alternatively, as in the illustrated embodiment, the longitudinal axis 92*a* of the screw channel 60 at the first end 64*a* does not match the longitudinal axis 92*b* of the screw channel 60 at the second end 64*b*. That is, the screw channel 60 is angulated. The longitudinal axis 92*b* of the screw channel 60 at the second end 64*b* is aligned with the overall longitudinal axis 18. The first opening 64*a* is situated at one of the sides of the component body 12.

Preferably, at least a portion 94 of the angulated screw channel 60 between the first opening 62*a* and the second opening 62*b* is curved.

In the screw channel 60, there is provided a screw seat 68 proximal to the second end 58*b*. The screw channel 60 preferably includes an inclined surface defining said screw seat 68. The screw seat 68 is adapted to seat the head 70 of a screw 72 (FIG. 4*b*) used for fixing the dental component 10 to the dental implant 46. Opposite the head 70, the screw 72 has an external thread 74. Also, when the component body 12 and the metal adapter 14 are assembled, the screw channel 60 of the component body 12 and the bore 28 of the metal adapter 14 are aligned.

When the dental component 10 is attached to the dental implant 18, the exposed region 42*a* of the metal adapter 14 of the dental component 10 is inserted into the implant 46 so that the at least one convex lobe 16 abuts against the corresponding concave recess(s) 44, as explained above. The screw 72 extends through the screw channel 60 and the bore 28, and further into the internally threaded portion 78, where the external thread 74 of the screw 72 engages said threaded portion 78. By turning the screw 72 with a suitable tool (not shown), the screw head 70 is pressed against the screw seat 68 in the component body 12, and the dental component 10 may be fixed to the implant 46. As the dental component 10 is attached to the dental implant 46, the metal adapter 14 is completely enclosed inside the component body 12 and the dental implant 46, as seen in FIGS. 4*a*-4*b*.

A suitable way of attaching the dental component 10 to the dental implant 46 is described in Applicant's co-pending application entitled "METHOD OF ATTACHING A DENTAL COMPONENT TO A DENTAL IMPLANT", the content of which herein is incorporated by reference.

The person skilled in the art realizes that the present invention by no means is limited to the preferred embodiments described above. On the contrary, many modifications and variations are possible within the scope of the appended claims.

The invention claimed is:

1. A dental component adapted to attach to a dental implant, the dental component comprising:
    a component body including at least one concave recess; and
    a metal adapter removably attachable to the component body,
    wherein the metal adapter includes at least one convex lobe adapted to abut against the at least one concave recess in the component body to prevent rotation between the component body and the metal adapter,
    wherein said at least one convex lobe extends apically of an apical end of the component body when the metal adapter is attached to the component body,
    wherein the metal adapter comprises at least one flexible arm with a protrusion adapted to press against a side wall or snap into any corresponding undercut of the component body to secure the metal adapter to the component body in the coronal-apical direction,
    wherein the at least one convex lobe and the at least one corresponding concave recess consist of three convex lobes and concave recesses uniformly distributed in the circumferential direction of the dental component, and
    wherein the at least one flexible arm consists of three flexible arms each having a protrusion, the three flexible arms being uniformly distributed in the circumferential direction of the dental component such that the each flexible arm is positioned between two of the convex lobes.

2. The dental component according to claim 1, wherein said at least one convex lobe is adapted to abut also against at least one corresponding concave recess in the dental implant to prevent rotation between the dental component and the dental implant.

3. The dental component according to claim 1, wherein the component body at its apical end has a recess including said at least one concave recess and said side wall, and wherein the recess is surrounded by a dental implant contacting surface.

4. The dental component according to claim 1, wherein the metal adapter is completely enclosed inside the component body and the dental implant.

5. The dental component according to claim 1, wherein the component body comprises a screw channel passing through the component body and forming a first opening at a first end and a second opening at an apical end, and a screw seat proximal to the apical end of the screw channel to seat the head of a screw for the fixation of the dental component to the dental implant.

6. The dental component according to claim 5, wherein a longitudinal axis of the screw channel at the first end does not match a longitudinal axis of the screw channel at the apical end.

7. The dental component according to claim 1, wherein the dental component is an abutment.

8. The dental component according to claim 1, wherein the component body is adapted to support a dental restoration.

9. The dental component according to claim 1, wherein the component body is a full-contour part.

10. The dental component according to claim 1, wherein the component body is ceramic.

11. The dental component according to claim 1, in combination with the dental implant.

12. A method of assembling a dental component adapted to attach to a dental implant, the dental component comprising: a ceramic component body including at least one concave recess, and a metal adapter according to claim 1 removably attachable to the ceramic component body the method comprising:

attaching the metal adapter to the ceramic component body so that the at least one convex lobe of the metal adapter abuts against the at least one concave recess in the ceramic component body, whereby said at least one convex lobe extends apically of an apical end of the ceramic component body to serve also as an interface to the dental implant.

13. The dental component according to claim 1, wherein the protrusion is adapted to press against the side wall and snap into any corresponding undercut of the component body.

\* \* \* \* \*